United States Patent [19]

Schaldach

[11] Patent Number: 5,632,770
[45] Date of Patent: May 27, 1997

[54] IMPLANTABLE DEFIBRILLATION SYSTEM WITH LEAD HAVING IMPROVED POROUS SURFACE COATING

[75] Inventor: Max Schaldach, Erlangen, Germany

[73] Assignee: Biotronik Mess-und Therapiegeraete GmbH & Co., Berlin, Germany

[21] Appl. No.: 403,703
[22] PCT Filed: Sep. 16, 1993
[86] PCT No.: PCT/DE93/00889
    § 371 Date: Mar. 17, 1995
    § 102(e) Date: Mar. 17, 1995
[87] PCT Pub. No.: WO94/06507
    PCT Pub. Date: Mar. 31, 1994

[30] Foreign Application Priority Data

Sep. 17, 1992 [DE] Germany .......... 42 31 600.6

[51] Int. Cl.$^6$ ................................. A61N 1/39
[52] U.S. Cl. ............ 607/122; 607/119; 607/129
[58] Field of Search ............... 607/119, 122, 607/129

[56] References Cited

U.S. PATENT DOCUMENTS

| | | | |
|---|---|---|---|
| 4,542,752 | 9/1985 | DeHaan et al. | 128/784 |
| 4,603,705 | 8/1986 | Speicher et al. | 607/122 |
| 4,784,160 | 11/1988 | Szilagyi | 128/784 |
| 4,784,161 | 11/1988 | Skalsky et al. | 607/122 |
| 4,817,634 | 4/1989 | Hollemann et al. | 128/784 |
| 4,969,463 | 11/1990 | Dahl et al. | 128/419 D |
| 5,016,645 | 5/1991 | Williams et al. | 607/129 |
| 5,090,422 | 2/1992 | Dahl et al. | 128/784 |
| 5,097,843 | 3/1992 | Soukup et al. | 128/784 |
| 5,111,812 | 5/1992 | Swanson et al. | 128/784 |
| 5,230,337 | 7/1993 | Dahl et al. | 607/119 |
| 5,269,810 | 12/1993 | Hull et al. | 607/129 |
| 5,271,417 | 12/1993 | Swanson et al. | 607/122 |
| 5,324,322 | 6/1994 | Grill, Jr. et al. | 607/118 |
| 5,374,287 | 12/1994 | Rubin | 607/122 |
| 5,411,544 | 5/1995 | Mar et al. | 607/122 |

FOREIGN PATENT DOCUMENTS

| | | | |
|---|---|---|---|
| E28126 | 2/1983 | Austria | 607/122 |
| 0043461 | 1/1982 | European Pat. Off. | 607/122 |
| 0064289 | 11/1982 | European Pat. Off. | 607/129 |
| 0115778 | 8/1984 | European Pat. Off. | 607/122 |
| 0211166 | 2/1987 | European Pat. Off. | 607/122 |
| 0426090 | 5/1991 | European Pat. Off. | 607/122 |
| 0453117 | 10/1991 | European Pat. Off. | 607/122 |
| 0458265 | 11/1991 | European Pat. Off. | 607/129 |
| 0475027A | 3/1992 | European Pat. Off. | 607/129 |
| 0475027 | 3/1992 | European Pat. Off. | 607/129 |
| 2643956 | 5/1977 | Germany | 607/129 |
| 3300672 | 7/1984 | Germany | 607/4 |
| 41122936 | 10/1991 | Germany | 607/122 |
| 4032153 | 4/1992 | Germany | 607/129 |
| 4207368 | 2/1993 | Germany | 607/122 |
| 4126363 | 2/1993 | Germany | 607/5 |
| 1357022 | 12/1987 | U.S.S.R. | 607/122 |
| 1722508 | 3/1992 | U.S.S.R. | 607/122 |

OTHER PUBLICATIONS

K. Stokes:"Implantable Pacing Lead Technology"; In: IEEE Engineering in Medicine and Biology Magazine, vol. 9, No. 2, Jun. 1990, New York, US, pp. 43–49.

E. Alt et al.: "A New Approach Towards Defibrillation Electrodes: Highly Conductive Isotropic Carbon Fibers"; In: Pacing and Clinical Electrophysiology, vol. 14, No. 11, Nov. 1991, Part II, pp. 1923–1928.

H. Makino et al.:"Implantable Defibrillator with High–Output Pacing Function After Defibrillation"; In: Proceedings of the IEEE, vol. 76, No. 9, Sep. 1988, pp. 1187–1193.

Primary Examiner—William E. Kamm
Assistant Examiner—Carl H. Layno
Attorney, Agent, or Firm—Spencer & Frank

[57] ABSTRACT

An implantable defibrillation system with an intercardial or subcutaneous defibrillation electrode is provided wherein the defibrillation electrode includes portions with a porous surface coating having an active surface area substantially larger than a surface area resulting from the basic geometrical shape of the electrode.

14 Claims, 3 Drawing Sheets

IMPLANTABLE DEFIBRILLATION SYSTEM WITH LEAD HAVING IMPROVED POROUS SURFACE COATING

BACKGROUND OF THE INVENTION

The invention relates to an implantable defibrillation system with an intracardial or subcutaneous defibrillation electrode.

What is known as ventricular fibrillation is a disturbance in heart rhythm which rapidly, as a consequence of the erratic contraction of individual muscle fibers and the resultant uncoordinated heart activity, leads to what is known as sudden cardiac death, unless defibrillation is done by suitable stimulation provisions. Such defibrillation is initially done externally, using suitable devices that produce high-energy pulses. For the sake of cardioversion, electrodes are applied to the chest of the patient and carry the pulses into the thorax.

Since such rescue provisions, using external devices and carried out by suitably trained helpers, often come too late for many patients, implantable defibrillators have since been created. They are provided with batteries and are implanted along with the electrodes in the body of the patient. If additional detection means are provided, which automatically trip defibrillating pulses upon the occurrence of ventricular fibrillation, then the affected patient can move about, even outside the range of medical assistance, without fear of possible danger from ventricular fibrillation that might occur.

Such implantable systems are still limited in their effectiveness and service life, however, by the high energy consumption in the defibrillation. Although the required energy can be reduced considerably in implanted devices compared with external devices, nevertheless the resultant useful life is short, especially if defibrillation is done frequently, and so reimplantation soon becomes necessary.

The difficulty in the choice of suitable endothoracic electrodes is that the electrodes must be embodied with the largest possible surface area, so that the stimulating current can be distributed over the entire affected region of the heart muscle. In contrast to the normal, pacemaking heart stimulation, defibrillating pulses after local excitation are not automatically propagated in the heart. Instead, provision must be made so that all the regions to be stimulated are located within the range of action of the stimulating current.

German Patent DE 26 43 956 C2 discloses a defibrillating electrode arrangement with large-area electrodes. It is intended for epicardial application and is meant to conform to the outline of the heart, with one of the electrodes conforming to the region of the apex of the heart and the other to the region of the upper heart.

One unfavorable aspect of these electrodes is that they still require a relatively large amount of energy, so that all the excitable cells of the heart can be depolarized. Moreover, the electrodes also have a certain intrinsic rigidity, which, if they do not move along with the surface of the heart, leads on the one hand to inadequate electrical contact of the heart muscle and on the other to a hindrance of the motion of the heart, since the electrodes involved are usually permanently stitched to the heart.

European Patent Disclosure EP 0 211 166 A2 also discloses an electrode that comprises a plurality of star-like or radiating electrode arms, which are secured to the surface of the heart. Once again there is the disadvantage that securing the individual electrode arms is relatively time-consuming. Moreover, securing them locally often does not accomplish the necessary distribution of current that must in fact be attained in the defibrillation.

One disadvantage of the known electrodes is that nevertheless, relatively large amounts of energy are still needed for the defibrillation, so that either very large energy reservoirs must be provided within the implantable housing—as a result of which, because of its large volume, in the final analysis the implant cannot be manipulated like a modern implanted cardiac pacemaker—or, if there is frequent recourse to the defibrillation function, then premature depletion of the energy reservoirs must be expected. This latter is especially disadvantageous in devices of the kind in which the defibrillation device is combined with a conventional cardiac pacemaker, because then if the battery is depleted, none of the life-sustaining functions will any longer be available.

SUMMARY OF THE INVENTION

The object of the invention, in an implantable defibrillation system of the generic type referred to at the outset, is to further increase the possible service life, that is, until the built-in energy source is depleted, by reducing the energy needed.

The above and other objects are accomplished in the context of an implantable defibrillation system of the type first mentioned above wherein, according to the invention, the defibrillation electrode includes portions with a porous surface coating having an active surface area substantially larger than a surface area resulting from the basic geometric shape of the electrode.

The invention includes the discovery that the electrode surface, as an interface with the tissue to be defibrillated—and therefore the material used—has special significance. While previously, the defibrillation energy to be transferred to the tissue was determined primarily by the impedance of the electrode surface, and thus—at comparable pulse amplitudes—the effective proportion of energy in the tissue was also relatively slight, with the novel embodiment of the electrode surfaces according to the invention the situation is that the transition resistance at the electrode surface is low compared with the tissue resistance. A higher proportion of the voltage is thus available for the defibrillation, and so—depending on the current or field distribution established in the tissue—larger regions of tissue are reachable by the defibrillation. It is thus also attained that even with electrodes of smaller surface area, defibrillation effects can be attained in tissue zones that previously required substantially larger electrode surfaces.

Because of the capability of changing the polarity, that is, the direction of the defibrillating current, when the defibrillation electrodes are connected, the rate of success of the defibrillations can be still further increased on a patient by patient basis.

The invention includes the discovery that the materials of the known electrodes, and particularly titanium, vanadium, zirconium and neobium, sometimes tend to extreme oxidation, and that this high tendency to oxidation upon contact with aqueous electrolytes means than a thin, insulating or semiconducting oxide film forms on the electrode surface; this film represents a capacitance $C_{ox}$ that is connected in series with the Helmholtz capacitance $C_H$ and thus to a slow decrease in total capacitance and hence to a corresponding increase in the defibrillation energy required at a given time. In anodic polarization, OH⁻ ions are pulled into the solid-state body, where they cause an increase in the oxide thickness. The result is a further decrease in the phase boundary capacitance and hence a further increase in the electrode impedance.

Thus because of their large relative surface area, the conventionally coated porous electrodes are fundamentally capable of defibrillation with good success at low energy. It was now found that the tendency to oxidation decreases the Helmholtz capacitance, which leads to an increase in the electrode impedance. The resultant influence on electrode properties in the course of the implantation time is quite grave because the worsening in electrode properties has effects that in turn contribute to an additional unfavorable effect on the defibrillating properties.

The long-term stable, biocompatible surface coating of the defibrillation electrode according to the invention comprises a material whose oxidation tendency is very slight; it is preferably applied by vacuum technology particularly vapor deposition such as reactive cathode sputtering (CVD, PVD or MOCVD) or ion plating, to the electrode, using an inert material, that is, a nitride, carbide, or carbonitride, or a pure element, alloy or compound selected from the group comprising the following materials: gold, silver, platinum, iridium and tellurium. A compound such as iridium nitride or iridium oxide could be used as the inert material. Because of the fractal three-dimensional geometry of a surface film applied in this way, its active surface area is very large, so that the quantity of energy required for the defibrillation can be kept slight. Applicant has found that by applying the surface coating according to the invention, the active surface area as a result of the fractal-like three dimensional geometry can be made greater by a factor of 1000 than the surface area resulting from the basic geometrical shape of the electrode.

The advantages of the defibrillation system according to the invention reside in particular in the large attainable capacitance of the electrode, which in turn means a substantial economy of energy in defibrillation. This is all the more signficant since in implantable systems, because of the energy reservoirs or battery cells that are also provided in the housing that must be implanted, the energy consumption should be kept especially low in order not to burden the patient with an overly large housing volume. An effective surface area of the electrode of approximately 100 cm$^2$ is advantageous. The energy given off in a defibrillation shock is only about 400 Ws, in the system according to the invention. The circumstance that the defibrillating pulses can be output with both polarities has an especially advantageous effect as well, since oxidation or redox reactions do not occur at the electrode surface. In this way, the reverse charge pulses of an output coupling capacitor can be utilized for defibrillation as well, which further contributes to additional energy savings.

BRIEF DESCRIPTION OF THE DRAWINGS

Other advantageous features of the invention are will be described in further detail below together with the description of the preferred embodiment of the invention, in conjunction with the drawings. Shown are.

DETAILED DESCRIPTION OF THE PREFERRED EMBODIMENTS

Figure 1:
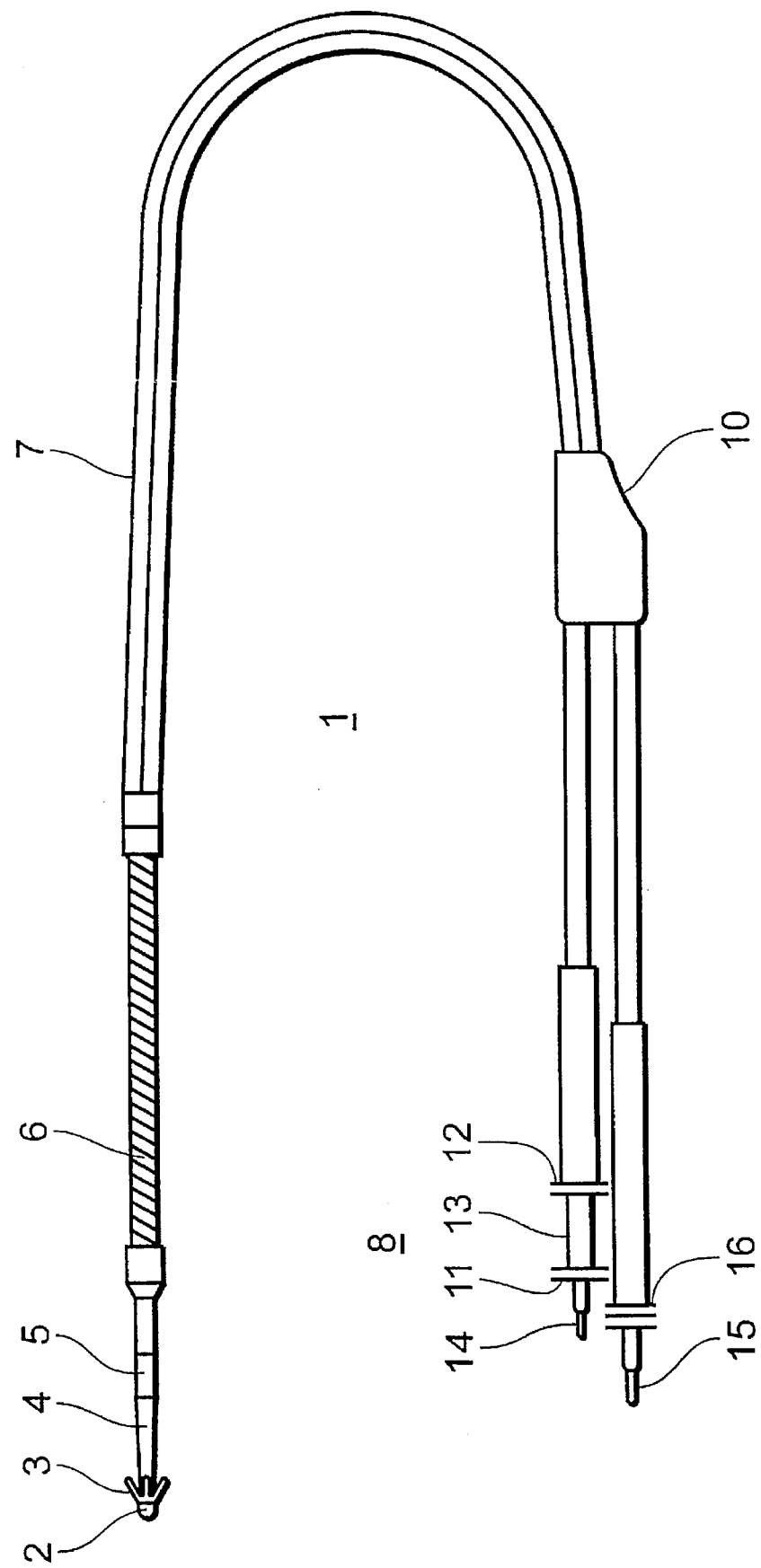
FIG. 1 a first exemplary embodiment of the defibrillation and pacemaker electrode according to the invention, for placement in the right ventricle.

The combined defibrillator-pacemaker electrode 1 shown in FIG. 1 comprises a conventional stimulating head, which has a stimulating and sensing face 2 on its distal tip, and securing elements 3, which are located slightly behind the stimulating and sensing face. An insulating region 4 is folowed by an adjoining reference electrode 5 for the bipolar stimulating system. This is followed by a helical shock coil 6 located approximately 25 mm behind the tip and extending over a range of 45 mm of the length of the distal electrode end. The outer diameter of the shock coil, which comprises a wire of PtIr 80/20 with a diameter of substantially 0.2 mm, is approximately 3 mm. The surface of the shock coil is provided with an iridium layer with a large surface area, which has a fractal surface geometry. The shock coil is adjoined by the insulated electrode supply lead 7, extending in which is a plurality of coaxial coils, each electrically connecting the contact regions 2, 4 and 6 with corresponding contact regions of plug elements 8 and 9. The supply lead itself is also surrounded by an insulating sheath. On the proximal end, a branching region 10 is provided that gives onto a pacemaker plug (plug element 8), which, between two encompassing radially oriented seals 11 and 12, has a contact region 13 that communicates with the reference electrode 5.

The free end 14 of the plug conversely communicates with the stimulating and sensing region 2 of the distal end. The shock coil 6 conversely communicates with a free end 15 of the plug element 9, and an elastic, radially operative, encompassing sealing region 16 is provided, in order, as in the sealing regions 11 and 12, to bring about a sealing off of the contact regions from body fluids when the plug elements are inserted into the pacemaker.

According to one preferred embodiment of the invention, the surface of the electrode, at least over a portion of its length, has wires or bundles or fibers in a regular arrangement, such that the electrode in this region has a substantially larger surface area than that corresponding to its geometrical basic shape. The portion of the electrode surface that has the wires or bundles of fibers has a plurality of wires or fiber bundles of different thickness, and in each case wires or fiber bundles of different thickness are adjacent to one another. Preferably, the wires or fiber bundles are coaxially coiled, around a flexible core.

Figure 2:
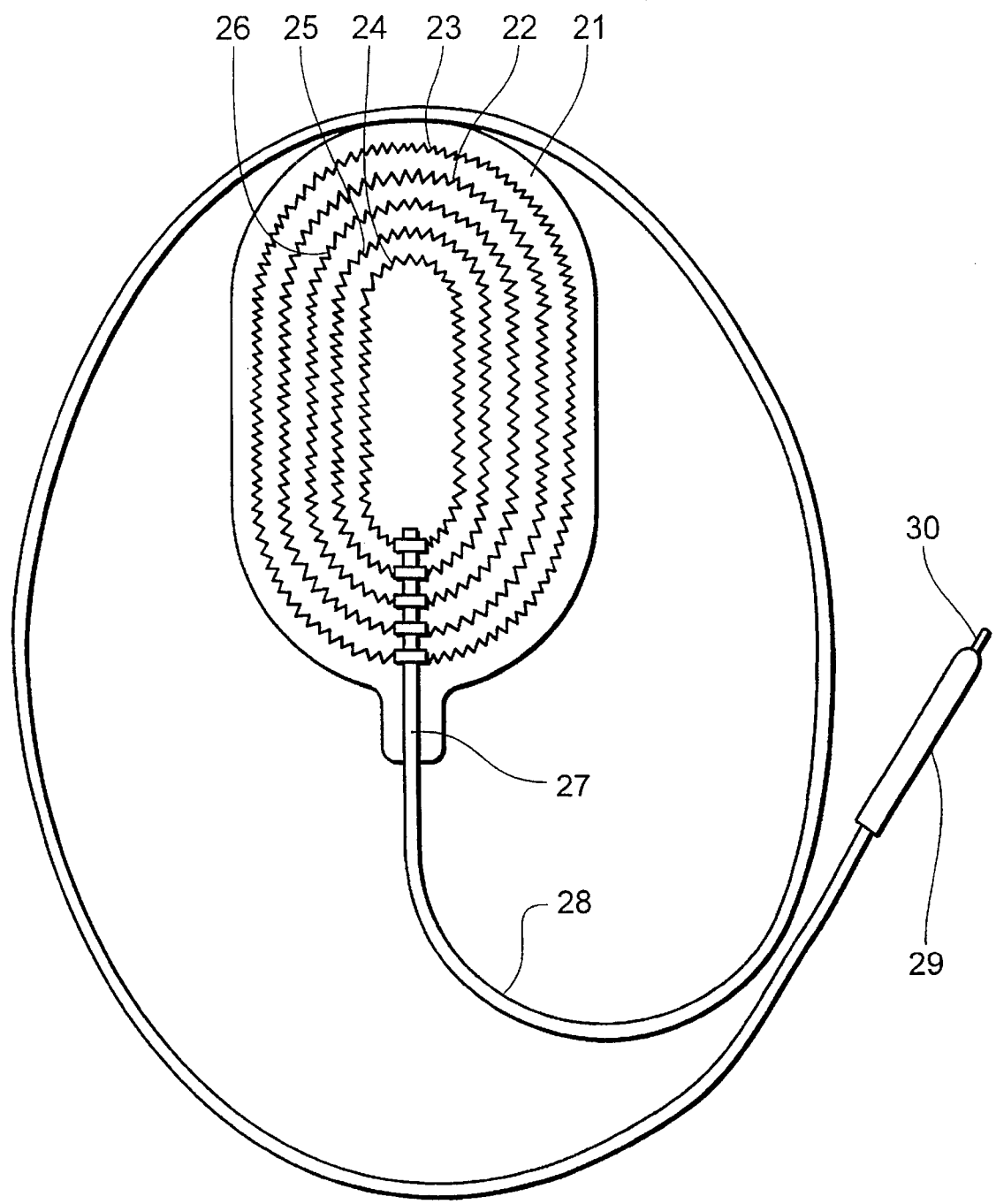
FIG. 2 a further exemplary embodiment of the electrode according to the invention, for subcutaneous or epicardial use.

FIG. 2 shows a further electrode, which on its distal end has a generally flat electrical contacting region 21 and is intended for being fastened to the epicardium. In an alternative use, this electrode may also be applied subcutaneously. A helical coil of a platinum-iridium alloy (PtIr 80/20) is embedded in a substrate of a physiologically compatible, elastic insulating material, in such a way that the predominant portion of the oval, concentrically extending coils 22–26 is accessible from outside for the purposes of electrical contacting. Securing the coils in the substrate material is done in such a way that a portion extending in the same direction of its peripheral region is enveloped by the material of the substrate in each case, which can be accomplished for instance by integral casting, extrusion-coating or the like. The surface of the electrode conductor is likewise coated with iridium, and in this respect one may refer to the other parts of the specification that describe this coating.

While the two outer oval-like rings 22 and 23 are embodied as double helixes, the three inner coils 23–26 of the exemplary embodiment shown are conceived of as single helixes. All the concentric oval coils 22–26 contact a connecting lead 27 that intersects the course of the coils in the middle of the semicircular arcs of the oval, on one end; this lead in turn communicates with a supply lead 28 that is completely sheathed with insulating material, and in which the supply lead coil extends and leads to a plug element 29, the free prong 30 of which is used to connect this electrode to the defibrillating part of the pacemaker.

Another electrode used in the stimulating system to be described here, for application in the superior vena cava is not shown in further detail, but in its design it is equivalent to the embodiment of FIG. 1; however, the stimulating part may be omitted, so that in this sense a shock coil is provided that forms the distal end of such an electrode and that communicates directly via a supply lead with a plug element 9, so that not only the stimulating and sensing face but also the plug element 8 provided for electrical contact of this face with the pacemaker may be omitted.

Figure 3:
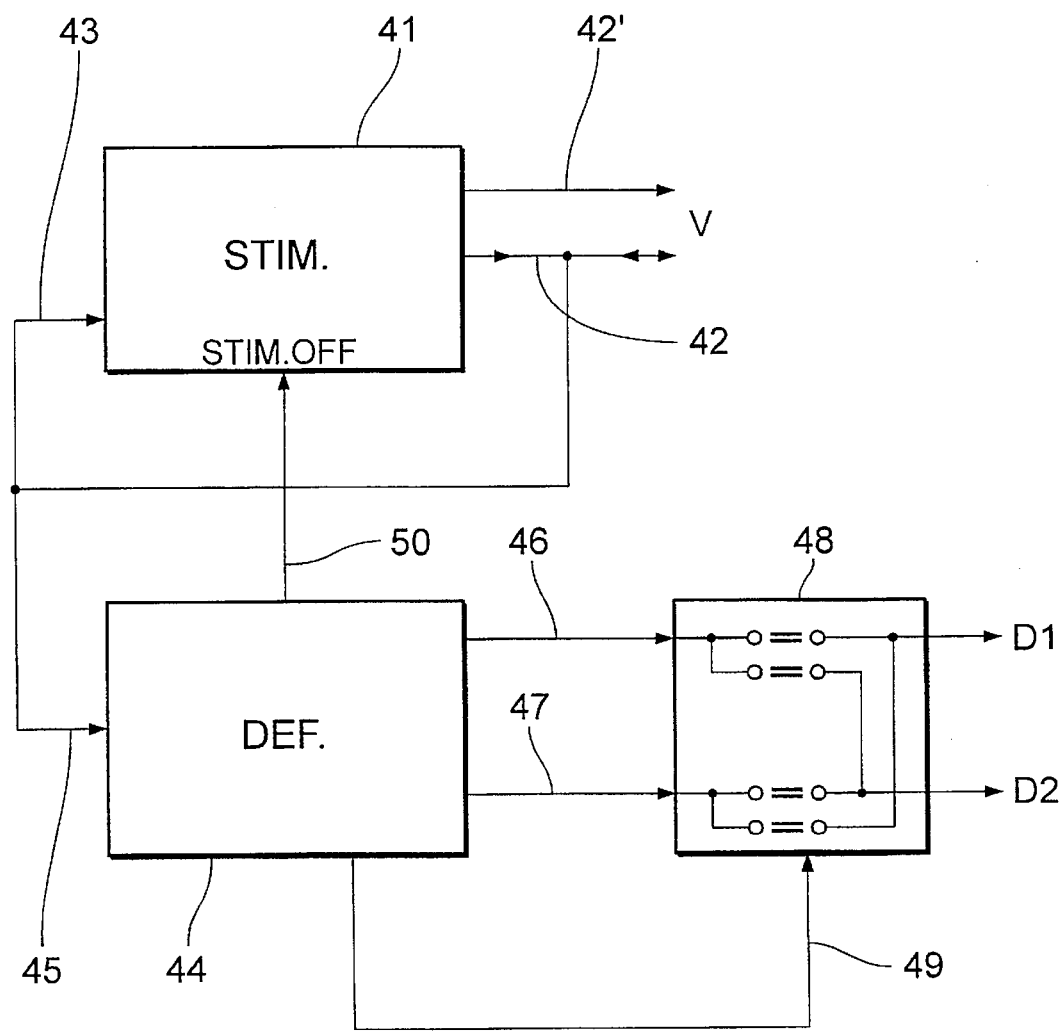
FIG. 3 a block circuit diagram of an implantable control part for a defibrillation system according to the invention.

FIG. 3, in a block circuit diagram, shows an implantable pacemaker/defibrillator that can be used in combination with the electrodes described above. A conventional pacemaker 41 has a terminal 42 (and in the case of bipolar stimulation the additional input 42' for the reference potential) and a sensing input 43, with which stimulating pulses can be output to the ventricle, or electrical signal phenomena occurring in the heart itself can be picked up. Besides the pacemaker system 41, a defibrillation system 44 is provided, to which the electrical signals picked up in the ventricle are likewise delivered, via a suitable input 45. On the output side, the defibrillation system 44 has two signal outputs 46 and 47, at which high-energy pulses for the defibrillation electrodes can be picked up. The two outputs 46 and 47 are followed by a reversing switch 48, which has internal switching means with which, in response to a corresponding input signal 49, the terminals of the defibrillation electrodes D1 and D2 can be transposed, so that a higher likelihood of success of the defibrillation can be selected by choosing the most favorable polarity of the electrode terminal for an individual patient.

The polarization reversal circuit 48 is controlled by a suitable output of the defibrillation system, over a signal line 49; an activation of this signal line brings about the transposition of the two terminals D1 and D2.

A defibrillation is tripped if ventricular fibrillation is detected via the input 45. In that case, an output signal is additionally output over a line 50, which additionally prevents the outputting of stimulating pulses by the pacemaker system 41 to the line 42.

The invention is not limited in its embodiment to the preferred exemplary embodiment described above. On the contrary, a number of variants are conceivable that make use of the invention shown and described, even if they are fundamentally different embodiments.

What is claimed is:

1. An implantable defibrillation system with an intracardial or subcutaneous defibrillation electrode, the improvement wherein the defibrillation electrode includes portions with a porous surface coating comprising one of an inert element, an inert chemical compound, and an inert alloy, the porous surface coating having a fractal three dimensional geometry and an active surface area that is greater by a factor of at least 1000 than a corresponding surface area resulting from the basic geometrical shape of the electrode.

2. The defibrillation system of claim 1, wherein the inert material comprises one of carbon, a nitride, carbide, carbonitride, and a pure element, alloy, or a compound of elements selected from the group comprising gold, silver, platinum, iridium and tellurium.

3. The defibrillation system of claim 1, wherein the coating comprises one of iridium, iridium nitride and iridium oxide.

4. The defibrillation system of claim 1, wherein the electrode has a base body of titanium.

5. The defibrillation system of claim 1, wherein the electrode comprises one of a myocardial and epicardial electrode for introduction through the superior vena cava.

6. The defibrillation system of one claim 1, wherein the electrode comprises part of a pacemaker electrode.

7. The defibrillation system wherein the surface coating is applied to the electrode by thin-film technology.

8. The defibrillation system of claim 7, wherein the surface coating comprises one of a reactive cathode sputtered (CVD, PVD or MOCVD) coating and an ion plated coating.

9. The defibrillation system of claim 7, wherein the surface coating comprises a vapor deposited coating.

10. The defibrillation system of claim 1, wherein the surface of the electrode, at least over a portion of its length, includes one of wires and bundles of fibers in a regular arrangement, such that the electrode in this region has a substantially larger surface area than that corresponding to its geometrical basic shape.

11. The defibrillation system of claim 10, wherein the portion of the electrode surface that has the wires or bundles of fibers has a plurality of wires or fiber bundles of different thickness, and in each case wires or fiber bundles of different thickness are adjacent to one another.

12. The defibrillation system of claim 10, wherein the wires or fiber bundles are coaxially coiled around a flexible core.

13. The defibrillation system of claim 10, wherein the portion of the electrode surface having the wires or fiber bundles has coaxially wound wire coils exhibiting a double-helix structure.

14. The defibrillation system of claim 10, wherein the portion of the electrode surface having the wires or fiber bundles has one of a spiral arrangement, meandering arrangement, and an arrangement formed of circles of different diameters, of the wires or fiber bundles, with a circular, oval or matlike outer contour.

* * * * *